United States Patent [19]

Dombrowski

[11] Patent Number: 4,653,513
[45] Date of Patent: Mar. 31, 1987

[54] BLOOD SAMPLER

[76] Inventor: Mitchell P. Dombrowski, 103 Mapleton, Grosse Point Farms, Mich. 48236

[21] Appl. No.: 764,051

[22] Filed: Aug. 9, 1985

[51] Int. Cl.⁴ .............................................. A61B 5/14
[52] U.S. Cl. .................................... 128/765; 128/770; 128/329 R
[58] Field of Search .................... 128/329 R, 763, 769, 128/765–767, 770; 604/51, 52, 156, 157, 180, 264, 272

[56] References Cited

U.S. PATENT DOCUMENTS

| | | | |
|---|---|---|---|
| 3,030,959 | 4/1962 | Grinert | 128/329 R |
| 3,208,452 | 9/1965 | Stern | 128/329 R |
| 4,203,446 | 5/1980 | Hofert et al. | 128/329 R |
| 4,360,016 | 11/1982 | Sarrive | 128/329 R |
| 4,380,234 | 4/1983 | Kamen | 604/180 |
| 4,421,123 | 12/1983 | Percupio | 128/765 |
| 4,462,405 | 7/1984 | Ehrlich | 128/329 R |
| 4,503,856 | 3/1985 | Cornell et al. | 128/329 R |
| 4,517,978 | 5/1985 | Levin et al. | 128/329 R |
| 4,535,769 | 8/1985 | Burns | 128/329 R |

Primary Examiner—Edward M. Coven
Assistant Examiner—Max F. Hindenburg
Attorney, Agent, or Firm—Reising, Ethington, Barnard, Perry & Milton

[57] ABSTRACT

A blood sampling device (10,10′) including a housing (12,12′) having an open end portion (16,16′) and an inner chamber (18,18′) adjacent to the open end portion (16,16′). A plunger (40,40′) is slidably mounted within the chamber (18,18′) for supporting a lancet (28,28′) having a lancet blade extending therefrom. The plunger (40,40′) is movable between a retracted position disposing the lancet blade (29,29′) away from the open end portion (16,16′) and an unretracted position disposing the lancet blade (29,29′) to extend beyond the open end portion (16,16′). The device (10,10′) includes a gasket (30,30′) for perfecting a seal between the housing (12,12′) and the plunger (40,40′) for creating a vacuum within the inner chamber (18,18′) when the plunger (40,40′) is moved from the unretracted position to the retracted position to thereby draw blood from the lanced skin.

28 Claims, 6 Drawing Figures

BLOOD SAMPLER

TECHNICAL FIELD

The subject invention relates to a blood sampling device adapted for self-administration.

BACKGROUND ART

The prevalence of diabetes has lately been increasing markedly in the westernized world. As of 1980, diagnosed diabetes represented approximately 2.8% of the U.S. population, although the actual total number of diabetes in the U.S. thought to exceed ten million.

The most important factor for reducing diabetes-associated complications is the maintenance of a tight glucose control, i.e. euglycemia. The maintenance of euglycemia may prevent and even reverse many of the sequelae of diabetes.

Presently, patients can monitor either their urine glucose or blood glucose. Urine glucose testing is essentially qualitative and not quantitative because the results represent an average blood glucose and additionally are affected by the renal glucose threshold. In contrast, frequent home glucose monitoring has been shown to have an excellent correlation with 24 hour blood glucose levels. A regular daily schedule of glucose monitoring allows patients to titrate their insulin dosages thereby achieving good control. After obtaining a droplet of blood, the glucose concentration may be determined with either test strips or a glucose meter. The article "Diabetes, the Comprehensive Self-Management Handbook" printed by Doubleday and Company of Garden City, N.Y., 1984, discusses in detail the goals and problems of self-testing of blood glucose. The major problem is that many diabetic patients intensely dislike to attempt blood glucose monitoring because a finger stick device must be used to obtain a drop of blood. The article discusses the use of automatic devices which help make the finger stick procedure easier. One such device is the Autolet which automatically performs the finger stick maneuver, the device being made by Owen Mumford Limited of England. The Autolet works as a lancet is fitted into a spring loaded arm. The arm is pulled back against the spring and secured in place by a lock. The finger is placed against the platform of the device. A button is pushed to release the lancet which automatically pricks the finger. Autoclix made by Bio-Dynamics works on the same principle. The lancet is hidden from hand and is released upon the pressing down of a button. A third device is the Monojector Lancet device, manufactured by Monoject Company.

The U.S. Pat. No. 4,203,446 to Hofert et al discloses a precision spring lancet which is automatically retracted back into the device after piercing a patients skin. The U.S. Pat. No. 4,360,016 to Sarrine discloses a blood collecting device having a lancet and a capillary tube carried together in a tubular housing. This device relies on capillary action for the removal of blood from the incision. The Hofert et al patent requires milking of blood from the pierced finger to force blood out through the incision.

The aforementioned devices utilize the piercing of a finger as the finger tip is highly vacularized and it is possible for the patient to "milk" the drop of blood from the finger tip. However, pain receptors have a very high concentration on the finger tips as compared to the forearm, trunk, buttocks, and upper thighs. Repeated blood samplings from small areas such as the finger tip results in the formation of scar tissue. Although the aforementioned automatic devices represent an improvement, they are still limited to the finger tips. They cannot be used on other body parts as the other body parts are not highly vascularized. Also, there is no way of milking a drop of blood from those areas.

The instant invention provides a device which can obtain a blood droplet from areas other than the finger tip such as the forearm, thigh or abdomen. This is advantageous since there are fewer pain fibers as well as much larger areas to sample from which avoids the formation of scare tissue on the fingers. Moreover, the utility of this device would not be limited to diabetes. For instance, it could be used in lieu of a heal-stick on neonates or whenever a small blood sample is needed from a patient.

STATEMENT OF THE INVENTION

According to the present invention, there is provided a blood sampling device including a housing having an open end portion and an inner chamber adjacent to the open portion. Lancet support means are sideably mounted within the chamber for supporting a lancet to extend therefrom. The lancet support means is moveable between a retracted position disposing the lancet support means away from the open end portion within the housing and an unretracted position disposing the lancet support means adjacent to the open end portion. Gasket means perfects a seal between the housing and the lancet support means and creates a vacuum within the inner chamber when the lancet support means is moved from the unretracted position to the retracted position.

FIGURES IN THE DRAWINGS

Other advantages of the present invention will be readily appreciated as the same becomes better understood by reference to the following detailed description when considered in connection with the accompanying drawings wherein.

DETAILED DESCRIPTION OF THE DRAWINGS

Figure 1:
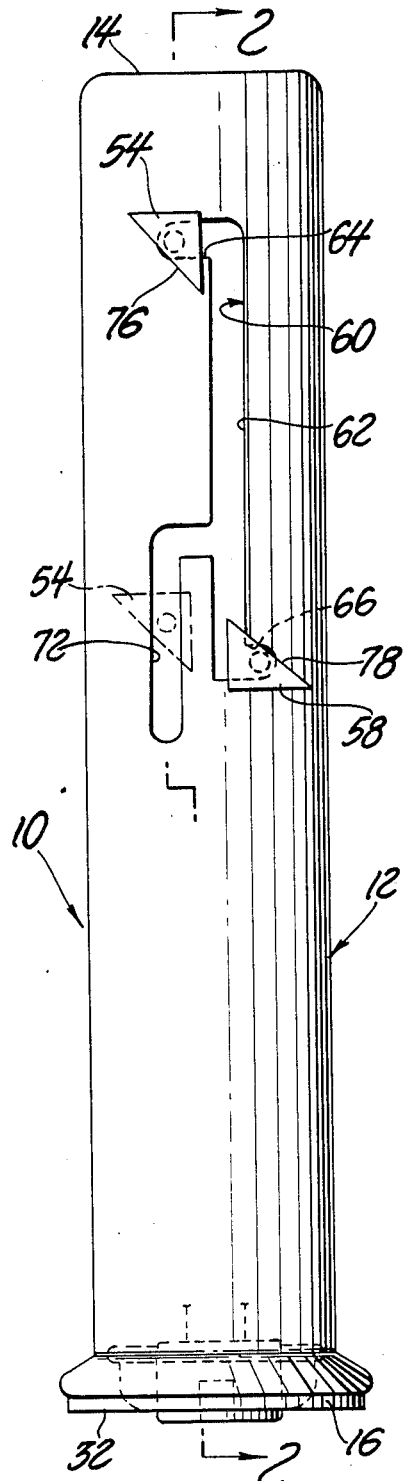
FIG. 1 is an elevational side view of a blood sampling device constructed in accordance with the instant invention.

A blood sampling device constructed in accordance with the instant invention is generally shown at 10 in the Figures. The devices 10 includes a housing generally indicated at 12 having a closed upper end 14 and an open lower end portion 16. The housing 12 includes an inner chamber defined by a substantially cylindrical inner wall 20 adjacent to the open end portion 16. The housing 12 includes a body portion 22 extending between the closed end portion 14 and open end portion 16. An inwardly radially extending wall 24 extends into the housing from the body portion 22.

Figure 2:
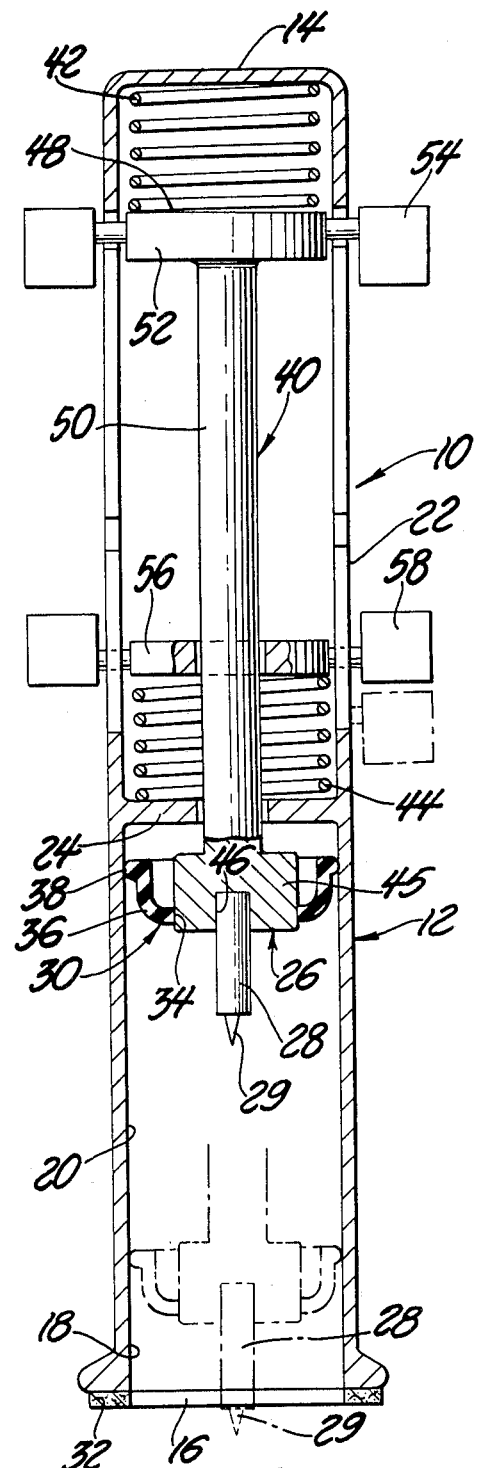
FIG. 2 is a cross sectional view taken substantially along lines 2—2 of FIG. 1.

The device 10 includes lancet support means generally indicated at 26 in FIG. 2. The lancet support means 26 is slidably mounted within the inner chamber 18 for supporting a lancet 28 therefrom. The lancet 28 may be removable and disposable, having a blade or tip 29 on the end thereof. The lancet support means 26 is movable between a retracted position as shown in the solid lines in FIG. 2 disposing the lancet support means 26 away from the open end portion 16 within the housing 12 and an unretracted position shown in hatch lines in FIG. 2 disposing the lancet support means 26 adjacent to the open end portion 16. When the lancet support means 26 is in the retracted position, the lancet blade 29 is contained completely within the housing 12. When the lancet support means 26 is moved to the unretracted position, the lancet blade 29 extends from the open end portion 16 of the housing 12.

The device 10 includes gasket means generally indicated at 30 for perfecting a seal between the housing 12 and the lancet support means 26 for creating a vacuum within the inner chamber 18 when the lancet support means 26 is moved from the unretracted position to the retracted position. The lancet support means 26 is moved to the unretracted position whereby the lancet blade 29 may pierce the skin of a patient. Upon retraction of the lancet support means 26, the lancet blade 29 is withdrawn into the housing 12 as a suction effect is created within the inner chamber 18 by the inter-action of the gasket means 30 with the inside wall 20 of the chamber 18. In this manner, a suction is created about the newly lanced skin thereby drawing lood out of the open cut. Less vascularized areas of skin, such as the buttocks, thigh or trunk, may be lanced and blood drawn therefrom. As these areas are less innervated with sensory nerve endings, it is significantly less painful to make such a cut thereby making the lancing operation more bearable for the patient. As these areas have significantly more surface area, the problem of scar tissue in a small area such as the finger tip is avoided.

More specifically, the open end portion 16 has a smooth peripheral surface defining a single plane. Being smooth, the open end portion 16 may perfect a seal with the skin in contact therewith. Sealing means 32 is mounted on the open end portion 16 for perfecting a seal between the open end portion 16 and a skin portion in contact therewith. The sealing means 32 may be made from a gasket material or other rubber or synthetic material to perfect a seal between the open end portion 16 and the contacted skin. The gasket means 30 and sealing means 32 interact to perfect a seal within the inner chamber 18 when the sealing means 32 is placed in contact with a patient's skin and the lancet support means 26 is moved to the retracted position.

The gasket means 30 includes a one way seal 30 for perfecting a seal when the lancet support means 26 is moved to the retracted position and for releasing the seal when moved to the unretracted position. The gasket means 30 includes a central portion 34 connected to the lancet support means 26. A flexible body portion 36 curves away from the open end portion 16 of the housing 12. A peripheral portion 38 is in contact with the inner wall 20. The peirpheral portion 38 is enlarged. The gasket means 30 fits within the inner chamber 18 so that the peirpheral portion 38 is biased against the wall 20 by the flexible body portion 36. Upon movement to the unretracted position, the peripheral portion 38 slides along the inner wall 20 without perfecting a seal, thereby allowing air to pass between the peripheral end portion 38 and inner wall 20. The shape of the gasket means 30 provides that a seal is perfected between the peripheral end portion 38 and inner wall 20 as the lancet support means 26 is moved in the opposite direction. In cooperation with the sealing means 32, the gasket means 30 causes a suction effect within the inner chamber 18 when the sealing means 32 is disposed against a patient's skin.

The device 10 includes biasing means for biasing the lancet support means 26 between the retracted and unretracted positions. More particularly, the lancet support means 26 includes a plunger member generally indicated at 40 slidably mounted within the housing 12. The biasing means includes a first spring 42 within the housing 12 for biasing the plunger member 40 to the unretracted position and a second spring 44 within the housing 12 for biasing the plunger member 40 to the retracted position. The plunger member 40 includes a lancet support end 45 proximate to the open end portion 16. The lancet support end 45 includes a lancet retaining pocket 46, the lancet 28 which maybe disposable being mounted therein. The plunger member 40 includes a second end 48 opposite to the lancet support end 45. A body portion 50 extends between the ends 45 and 48 of the plunger member 40.

The second end 48 of the plunger member 40 includes a radially outwardly extending flange 52. Levers 54 are mounted on the flange 52 and extend through the housing 12. A disc member 56 is disposed about the body portion 40, the disc member 56 extending radially outwardly from the body portion 40. A lever 58 is mounted on and extends radially outwardly from the disc member 56. The lever 58 extends through the housing 12. The levers 54 and 58 extend through a slot generally indicated at 60 in the housing, as shown in FIG. 1. The first spring 42 is disposed between the closed end 14 of the housing 12 and the first flange 52. The second spring 44 is disposed between the inwardly extending wall 24 of the housing 12 and the disc member 56. In other words, the first spring 42 abuts against the closed end portion 14 and the second spring 44 abuts against the inwardly extending wall 24. Preferably, the first spring 42 is a weaker spring for producing the forward motion of the plunger member 40 and the second spring 44 is a strong spring for moving the plunger member 40 to the retracted position and for producing the suction effect within the inner chamber 18.

The slot 60 more particularly includes a first slot portion 62 extending along a portion of the length of the housing 12. The first layer 54 is mounted on the first flange 52 and extends through the slot 60. The second lever 58 is mounted on the disc member 56 and extends through the slot 60.

The device 10 includes locking means for locking the first flange 52 against the biasing force of the first spring 42 thereby retaining the plunger member 40 in the retracted position. The locking means also locks the disc member 56 against the biasing force of the second spring 44. The locking means includes a second slot portion 64 and a third slot portion 66. The second and third slot portions 64,66 extend from and are perpendicular relative to the first slot portion 62. The levers 54 and 58 separate the flange 52 and disc member 56, respectively, when disposed in the second and third slots 64,66. In other words, the levers 54 and 58 are slidable along the first slot portion 62. As the lever 54 and associated flange 52 move longitudinally through the housing 12, the lancet support means 26 is moved from the retracted to unretracted positions.

In operation, the levers 54 and 58 are moved into the second and third slot portions 64,66 to lock the flange 52 and disc member 56 against the biasing force of the first and second springs 42,44 respectively. When the lever 54 is moved out of the second slot 64, the first spring member 42 biases against the flange 54 to force the plunger 40 from the retracted position to the unretracted thereby swiftly moving the lancet blade 29 to extend from the end of the open end portion 16 pierce the adjacent skin, as shown in phantom in FIG. 2.

The assembly 10 includes automatic release means for automatically releasing the second lever 58 from the locking mens when the lancet support means 26 is moved to the unretracted position thereby releasing the second spring 44 to bias the lancet support means 26 back to the retracted position. The automatic release means includes a first wedge portion defining an inclined surface 76 on the first lever 54 thereby being operatively connected to the first flange 52. A second wedge portion defined by an inclined surface 78 on the second lever member 58 is thereby operatively connected to the disc member 56. The disc member 56 is pivotally mounted about the body portion 50 whereby movement of the lancet support means 26 to the unretracted position causes the first wedge surface 76 to contact the second wedge surface 78 thereby rotating the disc member 56. As the disc member 56 rotates, the second lever 58 is moved out of the third slot portion 66 so as to release the second disc member 56 from the locking means. Alternatively, the wedge surfaces 76,78 may be in the form of projections facing downwardly from the flange 52 and upwardly from the flange 56, the wedges coacting to rotate the disc member 56 upon contact of the two wedges. Upon movement of the second lever 58 from the third slot portion 66, the second spring 44 forces the disc member 56 against the flange 52 so as to force the plunger 40 into the retracted position. The movement of the plunger 40 draws the lancet blade 29 out of the cut. As the plunger 40 moves to the retracted position, a vacuum is created within the inner chamber 18 by the cooperative effect of the gasket means 30 and sealing means 32. A droplet of blood is withdrawn from the cut and a blood sample may be taken therefrom.

The lancet support means 26 has a loading position, as shown in FIG. 1. In the loading position, the lancet support means 26 extends to the open end portion 16. The device 10 further includes a fourth slot portion 72 extending from the first slot portion 62. The fourth slot portion 72 is parallel relative to the first slot portion 62. The fourth slot portion 72 receives the first lever 54 as the lancet support means 26 is moved to the loading position. Once loaded, the first lever 54 is returned to its locked position in slot 64 and the second lever is maintained in its locked position in slot 66. The disposable lancet 28 is replaced with the support means 26 disposed in the fully extended position as shown in hash lines in FIG. 1.

A second embodiment of the instant invention is shown in FIGS. 3-6. Like primed numerals are used to indicate like structure between the several embodiments.

Generally, the device 10' includes a housing generally indicated at 12' having an open end portion 16' and an inner chamber 18' adjacent to the open end portion 16'. The plunger 40' is slidably mounted within the chamber 18' for supporting a lancet 28' to extend therefrom. The plunger 40' includes a handle 82, a body portion 50' and an end portion 48' and amounting portion 45' including a slot 46' wherein the disposable lancet blade 29' is mounted. The plunger 40' is movable between a retracted position disposing the lancet blade 29' away from the open end portion 16' and an unretracted position disposing the lancet 28' to extend beyond the open portion 16'. The device 10' includes a gasket 30' for perfecting a seal between the housing 12' and the plunger 40' for creating a vacuum within the inner chamber 18' when the plunger 40' is moved from the unretracted position to the retracted position to thereby draw blood from the lanced skin. The housing 12' includes a radially inwardly extending wall portion 24'. The first spring 42' is held in tension between the wall portion 24' and the flange 52' and the second spring 44' is held in compression between the disc member 56' and the wall portion 24'.

The open end portion 16' may have a removable tightly fitting annular cap 85 mounted thereon. The cap 85 is centrally open, and has the mounted sealing means 32' mounted thereon. Such a removable cap 85 may be made of varying thickness such that the depth of incision by the lancet blade 29 may be controlled by placing a thinner or thicker cap onto the open end portion 16'. The size of the opening may also be varied.

The assembly 10' includes housing biasing means for biasing apart the outer and inner housing portions 92,96. The housing biasing means includes spring 112 disposed between the radially inwardly extending wall 80 of the outer housing 92 and the bottom wall 98 of the inner housing 96.

Figure 3:
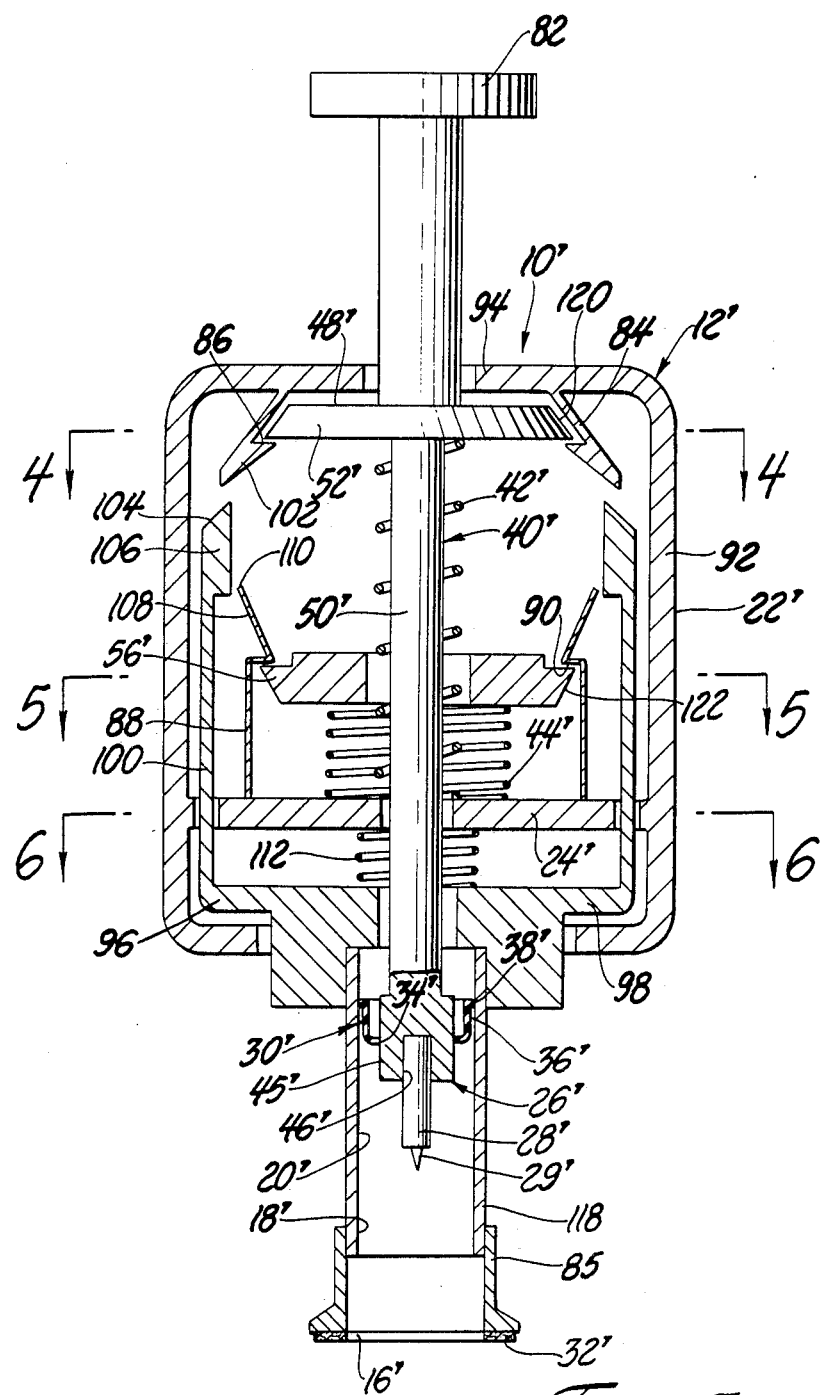
FIG. 3 is a cross sectional view of a second embodiment of the instant invention.

As in the first embodiment, the assembly 10' includes locking means for locking the flange 52' against the biasing force of the first spring 42' and locking the disc member 56' against the biasing force of the second spring 44'. The locking means includes a pair of flexible arms 84, each of the arms 84 including a shoulder 86 abutting against the flange 52', as shown in FIG. 3, for retaining the flange 52' against the biasing force of the first spring 42'. The housing 12' includes a second pair of flexible arms 88, each of which having a second shoulder 90 abutting against the disc member 56' for retaining the disc member 56' against the biasing force of the second spring 44'.

The assembly 10' includes automatic release means for automatically releasing the flange 52' and disc member 56' from the locking means. More specifically, the housing 12' includes an outer portion 92 including an upper wall 94 of the housing 12'. The upper wall 94 includes the first flexible arms 84 extending substantially downwardly therefrom. The radially inwardly extending wall portion 24' extends inwardly from the outer housing portion 92. The housing 12' further includes an inner moveable portion generally indicated at 96 including a bottom wall 98. Two inwardly extending portions or arms 100 extend upwardly from the bottom wall 98.

The outer portion 92 of the housing 12' is movable relative to the inner portion 98. The automatic release means includes an inclined lower surface 102 of the first arm 84 and an inclined upper surface 104 of the upwardly extending portions 100. When the open end portion 16' of the invention is pressed firmly against the skin, the outer housing 92 is moved to abut the inclined surfaces 102,104 and outwardly flex the first arms 84 for releasing the flange 52' from abutment with the shoulder 86 of the first arms 84. The first arms 84 are forced to flex outwardly as they are engaged by the upwardly extending portions 100. More specifically, the upwardly extending portions 100 have an enlarged end portion 106, the upper surface of which defines the inclined surfaces 104. The second arms 88 have an inclined upper surface 108 above the shoulders 90. The edge 110 of the inclined surface 108 no longer abuts against the enlarged portion 106 of the upwardly extending portions 100 as the inclined surface 102 of the arms 84 are brought into abutment with the inclined surface 104 of the upwardly extending portions 100. Therefore, when inclined surfaces 102 and 104 abut each other, the enlarged portion 106 of arms 100 are no longer adjacent to and therefore do not prevent the arms 88 from potential lateral displacement.

The automatic release means further includes the upper inclined surface 108 on the second arms 88. The first flange 52' has a radially peripheral corner for contacting the upper inclined surface 108 of the second arms 88. When surface 104 of arms 100 are in contact with arms 84, the enlarged portion 106 is no loner adjacent to edge 110. Since the edge 110 no longer abuts the thickened portion 106, the peripheral corner of flange 52' is able to radially outwardly deflect arms 88 thereby releasing the disc member 56' from the shoulder 90 of the second arms 88. Upon release, the disc member 56' is biased upwardly by the second spring 44' to return the plunger 40' to the retracted position.

Figure 4:
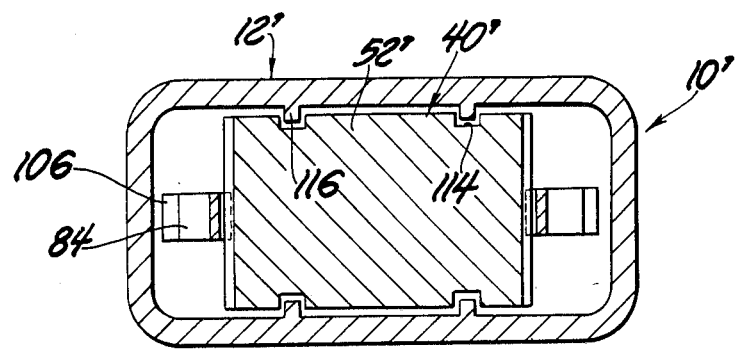
FIG. 4 is a cross sectional view taken substantially along lines 4—4 of FIG. 3.
Figure 5:
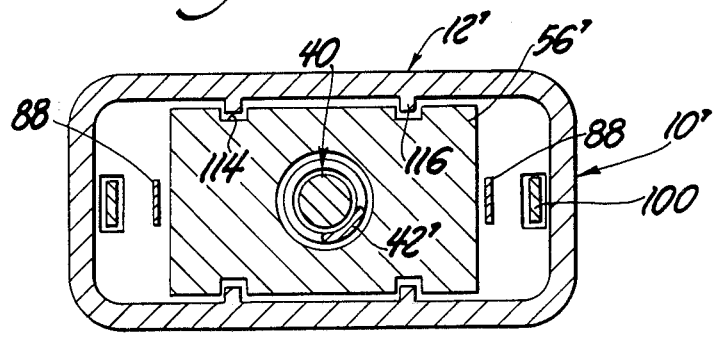
FIG. 5 is a cross sectional view taken substantially along lines 5—5 of FIG. 3.
Figure 6:
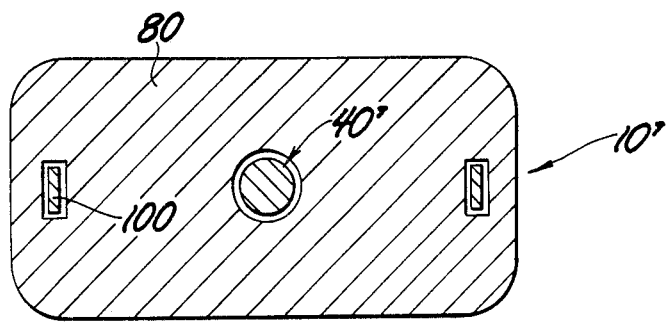
FIG. 6 is a cross sectional view taken substantially along lines 6—6 of FIG. 3.

The device 10' includes alignment means for aligning the flange 52' during movement of the lancet support means 26' between the retracted and unretracted positions. As shown in FIGS. 4 and 5, the flange 52' includes a plurality of peripheral recesses 114. The alignment means includes a plurality of ribs 116 seated within the recesses 114.

In operation, the plunger has moved so that the lancet 28' is in the retracted position within a tubular housing 118 supported from the bottom weall 98 of the inner housing 96, the tubular member 118 defining the inner chamber 118. In the retracted position, as shown in FIG. 3, the upper flange 52' is retained in by the shoulders 86 of the arms 84 against the biasing force of the first spring 42'. The disc member 56' is retained against the biasing force of the second spring 44' by the shoulders 90 of the second arms 88. The gasket 32' is brought in contact with patient's skin. The outer housing 92 is forced downwardly towards the patient's skin relative to the inner housing 96 so as to bring the inclined surface 102 into abutting contact with the upper inclined surface 104. As previously explained, the first arms 84 are flexed outwardly thereby releasing the first flange 52. The first spring 42' draws the first flangew 52', plunger, 40' and accordingly the lancet 28' to the unretracted position. The lancet would cut the patient's skin as it is drawn beyond the outer end portion 16' of the tubular member 118. As the lancet 28' becomes fully extended, the peripheral corner of the flange 52' contacts the inclined surface 108 of the second arms 88 thereby outwardly moving the second arms 88 to release the disc member 56'. The second spring 44' biases the unlocked disc member 56' upwardly thereby upwardly forcing the flange 52' and plunger 40' therewith. The lancet blade 29' is drawn out of the cut and a suction is created by the gasket means 30' in combination with the gasket means 32' to draw blood from the pierced skin. In order to load a new lancet 28' in the assembly 10', the plunger 40' is moved downwardly so that the disc member 56' is moved towards the inwardly extending wall 24 and the flange member 52' is brought in below the shoulder 90 of the second arms 88. Once the flange 52' is moved below the shoulder 90, the end portion 45' of the plunger 40' is exposed from below the end portion 16' of the housing 12'. The lancet 28' may then be removed and replaced. The flange 52' has an upper incline shoulder 120 which is not engaged by the shoulder 90 thereby releasing the flange 52 from the second arms as the plunger 40' is moved back towards the retracted position. In other words, the upwardly inclined surface 120 of the flange 52' is not retained by the shoulder 90. In this condition, the shoulder 90 is now not radially deflected by flange 52' since the edge 110 abuts enlarged portion 106 and thereby does not allow lateral deflection of arms 88 and its shoulder 90 to lock and retain disc 56' in the retracted position. To cock the invention ready for use, tension is placed on spring 52' by gripping and pulling on handle 82 until flange 52' locks against arms 84. Likewise, the disc member 56' has an inclined surface 122 which allows the disc member 56' to be reloaded into the locked position as it will react with the inclined surface 108 of the second arms 88 to outwardly bias the second arms 88 when the disc member 56 is moved to locked position.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A blood sampling device (10,10') comprising: a housing (12,12') including an open end portion (16,16') and an inner chamber (18,18') adjacent to said open end portion (16,16'); lancet support means (26,26') slidably mounted within said inner chamber (18,18') for supporting a lancet (28,28') to extend therefrom, said lancet support means (26,26') being movable between a retracted position disposing said lancet support means (26,26') away from said open end portion (16,16') within said housing (12,12') and an unretracted position disposing said lancet support means (26,26') adjacent to said open end portion (16,16') for receiving a lancet and thereafter making an incision in the skin of a patient; and characterized by gasket means (30,30') movable with said lancet support means (26,26') for perfecting a fluid seal between said housing (12,12') and said lancet support means (26,26') to prevent fluid flow past said gasket means (30, 30') during movement toward said retracted position, said open portion (16,16') presenting sealing means (32,32') to perfect a seal between said open end portion (16,16') and a portion of skin in contact therewith for creating a vacuum within said inner chamber (18,18') when said lancet support means (26,26') and said gasket means (30,30') are moved from said unretracted position to said retracted position, and biasing means for moving said lancet support means (26,26') from said retracted position to said unretracted positions so that said open end portion (16,16') may be placed in sealing engagement with a portion of skin and said lancet support means (26,26') supporting a lancet may be moved with said gasket means (30,30') by said biasing means to said unretracted position to pierce the skin with the lancet and draw a blood sample out of the incision as a result of the vacuum created by moving said gasket means (30,30') weith said lancet support means (26,26') back toward said retracted position.

2. A device as set forth in claim 1 further characterized by said open end portion (16,16') having a smooth peripheral surface defining a single plane.

3. A device as set forth in claim 2 further characterized by said biasing means being positioned to move said lancet support means and said gasket means from said unretracted position causing the incision back toward said retracted position to remove the lancet from the incision.

4. A device as set forth in claim 1 further characterized by said skin sealing means (32,32') including a gasket material mounted on said open end portion (16,16').

5. A device as set forth in claim 1 further characterized by including a removable cap member (85) mounted on said open end portion (16,16') and having a central opening.

6. A device as set forth in claim 2 further characterized by said gasket means (30,30') including a one way seal (30,30') for perfecting a seal when said lancet support means (26,26') is moved to said retracted position and for releasing said seal when said lancet support means (26,26') is moved to said unretracted position.

7. A device as set forth in claim 6 further characterized by said housing, (12,12') having an inner wall (20,20') containing said inner chamber (18,18'), therewithin said gasket means (30,30') including a central portion (34,34') connected to said lancet support means (26,26') and a flexible body portion (36,36') curving away from said open end portion (16,16') and a peripheral portion (38,38') in contact with said inner wall (20,20').

8. A device as set forth in claim 7 further characterized by said gasket means (26,26') having an enlarged peripheral portion (38,38') relative to said central portion (34,34').

9. A device as set forth in claim 8 further characterized by said lancet support means (26,26') including a plunger member (40,40') slidably mounted within said housing (12,12'), said biasing means including a first spring (42,42') for biasing said plunger member (40,40') to said unretracted position and a second spring (44,44') within said housing (12,12') for biasing said plunger member (40,40') to said retracted position.

10. A device as set forth in claim 9 further characterized by said plunger member (40,40') including a lancet support end (45,45') proximate to said open end portion and a second end (48,48') opposite thereto and a body portion (50,50') extending therebetween, said second end (48,48') including a radially outwardly extending flange (52,52'), and said device (10,10') including a radially outwardly extending disc member (56,56') disposed about said body portion (50,50'), said first spring (42,42') being disposed between said housing (12,12') and said first flange (52,52') and said second spring (44,44') being disposed between said housing (12,12') and said disc member (56,56').

11. A device as set forth in claim 10 further characterized by said housing (12) including a closed end portion (14) opposite to said open end portion (16) and a radially inwardly extending wall (24) therebetween, said first spring (42) abutting said closed end portion (14) and said second spring (44) abutting said inwardly extending wall (24).

12. A device as set forth in claim 11 further characterized by said housing (12) including a slot (60) having a first slot portion (62) extending along a portion of the length thereof, said device (10) further including a first lever (54) mounted on said first flange (52) and extending through said slot (60) and a second lever (58) mounted on said disc member (56) and extending through said slot (60).

13. A device as set forth in claim 12 further characterized by including locking means for locking said flange (52) against the biasing force of said first spring (42) and locking said disc member (56) against the biasing force of said second spring (44).

14. A device as set forth in claim 13 further characterized by said locking means including second and third spaced slot portions (64,66) extending from and being perpendicular relative to said first slot portion (62), said first and second lever (54,58) separating said flange (52) and disc member (56), respectively, when disposed in said second and third slot portions (64,66).

15. A device as set forth in claim 14 further characterized by said lancet support means (26) having a loading position wherein said lancet support means (26) extends to said open end portion (16), said device (10) further including a forth slot portion (72) extending from said first slot portion (62) and being parallel relative thereto for receiving said first lever (54) as said lancet support means (26) is moved to said loading position.

16. A device as set forth in claim 13 further characterized by automatic release means for automatically releasing said second lever (58) from said locking means when said lancet support means (26) is moved to said unretracted position thereby releasing said second spring (44) to bias said lancet support means (26) back to said retracted position.

17. A device as set forth in claim 16 further characterized by said automatic release means including a first wedge (76) operatively connected to said first flange (52) and a second wedge (78) operatively connected to said disc member (56), said disc member (56) being pivotally mounted about said body portion (50) whereby movement of said lancet support means (26) to said unretracted position causes said first wedge (76) to contact said second wedge (78) to rotate said disc member (56) thereby moving said second lever (58) out of said third slot portion (66) and releasing second disc member (56) from said locking means.

18. A device as set forth in claim 17 further characterized by said first lever (54) including said first wedge (76) and said second lever (58) including said second wedge (78).

19. A device as set forth in claim 10 further characterized by said housing (12') including a radially inwardly extending wall portion (24'), said first spring (42') being held in tension between said wall portion (80) and said flange (52') and said second spring (44') being held in compression between said disc member (56') and said wall portion (80).

20. A device as set forth in claim 19 further characterized by including locking means for locking said flange (52) against the biasing force of said first spring (42') and locking said disc member (56') against the biasing force of said second spring (44').

21. A device as set forth in claim 20 further characterized by said locking means including at least one flexible first arm (84) having a first shoulder (86) abutting against said flange (52') for retaining said flange (52') against the biasing force of said first spring (42') and at least one flexible second arm (88) having a second should (90) abutting against said disc member (56') for retaining said disc member (56') against the biasing force of said second spring (44').

22. A device as set forth in claim 21 further characterized by said housing (12') including an outer portion (92) including an upper wall (94) of said housing (12'), said upper wall (94) including said first flexible arm (84) extending substantially downwardly therefrom and said radially inwardly extending wall portion (214'), said housing (12') further including an inner portion (96) including a bottom wall (98) and at least one upwardly extending portion (100), said outer portion (92) being movable relative to said inner portion (98).

23. A device as set forth in claim 22 further characterized by said automatic release means including an inclined lower surface (102) of said first arm (84) and including an upper surface (104) of said upwardly extending portion (100), said outer housing (92) being movable to abut said inclined surfaces (102,104) and outwardly flex said first arm (84) for releasing said flange (52') from abutment with said shoulder (86) of said first arm (84).

24. A device as set forth in claim 23 further characterized by said automatic release means including an upper inclined surface (108) on second second arm (88), said first flange (52') having a radially peripheral corner for contacting said upper inclined surface (108) of said second arm (88) and moving said second arm (88) radially outwardly to and releasing said disc member (56') from said shoulder (90) of said second arm (88).

25. A device as set forth in claim 24 further characterized by including housing biasing means for biasing apart said outer and inner housing portions (92,96).

26. A device as set forth in claim 25 further characterized by said housing biasing means including a spring (112) disposed between said radially inwardly extending wall (80) of said outer housing (92) and said bottom wall (98) of said inner housing (96).

27. A device as set forth in claim 25 further charcterized by including alignment means for aligning said flange (52') during movement of said lancet support means (26') between said retracted and unretracted positions.

28. A device as set forth in claim 27 further charcterized by said flange (52') including a plurality of peripheral recesses (114), said alignment means including a plurality of ribs (116), seated within said recesses (114).

* * * * *